(12) United States Patent
Ingimarsson

(10) Patent No.: US 6,589,289 B2
(45) Date of Patent: Jul. 8, 2003

(54) PROSTHETIC SOCKET AND SOCKET COMPONENT ASSEMBLY

(75) Inventor: Gudni Ingimarsson, Reykjavik (IS)

(73) Assignee: Ossur hf (IS)

( * ) Notice: Subject to any disclaimer, the term of this patent is extended or adjusted under 35 U.S.C. 154(b) by 0 days.

(21) Appl. No.: 09/969,594

(22) Filed: Oct. 4, 2001

(65) Prior Publication Data
US 2002/0042659 A1 Apr. 11, 2002

Related U.S. Application Data

(60) Provisional application No. 60/237,381, filed on Oct. 4, 2000.

(51) Int. Cl.[7] .............................. A61F 2/80; A61F 2/62
(52) U.S. Cl. ........................................... 623/33; 623/38
(58) Field of Search ..................................... 623/32–38

(56) References Cited

U.S. PATENT DOCUMENTS

| | | | |
|---|---|---|---|
| 4,134,159 A | 1/1979 | Wilson | |
| 4,221,007 A | 9/1980 | Wilson | |
| 5,201,774 A | 4/1993 | Greene | |
| 5,464,443 A | 11/1995 | Wilson et al. | |
| 5,824,110 A | 10/1998 | Rothschild et al. | |
| 5,888,217 A | * 3/1999 | Slemker | 623/36 |
| 5,928,290 A | 7/1999 | Gramnas | |
| 5,980,576 A | * 11/1999 | Graf et al. | 623/33 |
| 6,093,210 A | * 7/2000 | Gramnas | 623/33 |
| 6,106,559 A | * 8/2000 | Meyer | 623/33 |
| 6,267,787 B1 | * 7/2001 | Capper et al. | 623/36 |
| 6,287,345 B1 | * 9/2001 | Slemker et al. | 623/34 |

* cited by examiner

Primary Examiner—David H. Willse
Assistant Examiner—Suzette J. Jackson
(74) Attorney, Agent, or Firm—Bacon & Thomas, PLLC

(57) ABSTRACT

A prosthetic socket includes a recess at its distal end for receiving a prosthetic socket component such as a pin interlock device and a threaded opening providing access to the recess from the inside of the socket. A threaded retainer may be threadedly fastened to the threads of the opening for removably retaining the prosthetic socket component within the recess.

12 Claims, 5 Drawing Sheets

PROSTHETIC SOCKET AND SOCKET COMPONENT ASSEMBLY

This application claims the benefit of Provisional Patent Application Ser. No. 60/237,381, filed Oct. 4, 2000.

BACKGROUND OF THE INVENTION

1. Field of the Invention

This invention relates to prosthetic sockets having an integrated prosthetic socket component retainer feature.

2. Related Technology

Molded prosthetic sockets arranged to receive residual limbs of amputees and including prosthetic socket components such as interlocks for securing the sockets to a prosthetic device are described in U.S. Pat. No. 5,464,443 granted Nov. 7, 1995 and U.S. Pat. No. 5,824,110 granted Oct. 20, 1998.

Various other prosthetic socket components such as a valve or torque absorber associated with such prosthetic sockets are described in U.S. Pat. No. 5,201,774 granted Apr. 13, 1993 and U.S. Pat. No. 4,134,159 granted Jan. 16, 1979.

Various prosthetic socket components are typically connected to the closed end of the socket to enable the socket to be connected to a prosthetic device or to otherwise facilitate the use of the prosthetic socket. For example, the aforesaid U.S. Pat. No. 5,464,443 shows a serrated post or pin associated with a flexible liner that is received within an interlock device so that the liner, which contains the residual limb of an amputee, may be interlocked with the prosthetic device connected to the closed end of the socket.

The aforesaid U.S. Pat. No. 5,201,774 describes a valve system molded integrally into a prosthetic socket.

In accordance with known prior art, such prosthetic socket components are typically molded integrally into the prosthetic socket or are secured to the exterior thereof by means of suitable fasteners that may be removable to permit replacement of the prosthetic socket component, for example a pin interlock system or a valve.

It is highly desirable to simplify the incorporation of a prosthetic socket component such as a pin interlock, a valve device, lanyard arrangement or other component into the distal end of a prosthetic socket whereby the component may be removably secured within the distal end of the prosthetic socket using a retainer assembly that is removably secured to the distal end of the prosthetic socket.

BRIEF SUMMARY OF THE DISCLOSURE

In accordance with a preferred embodiment of the invention, the distal end of a prosthetic socket is molded in a manner that provides a recess for receiving a prosthetic socket component and the distal end of the prosthetic socket is provided with an opening providing access to the recess. The opening is provided with integral threads or other connector feature molded or secured therein into which is threaded or connected a retainer that effectively retains a prosthetic socket component within the recess. The retainer is selectively removable to enable replacement of the prosthetic socket component in a simple and convenient manner.

Alternatively, different adapters can be secured to the prosthetic socket. Such adapters accommodate different types of prosthetic devices such as those having pyramid-type and four-hole attachment systems.

DESCRIPTION OF THE DRAWINGS

The invention will be better understood with reference to the appended drawings wherein.

DETAILED DESCRIPTION OF PREFERRED EMBODIMENTS OF THE INVENTION

Figure 1:
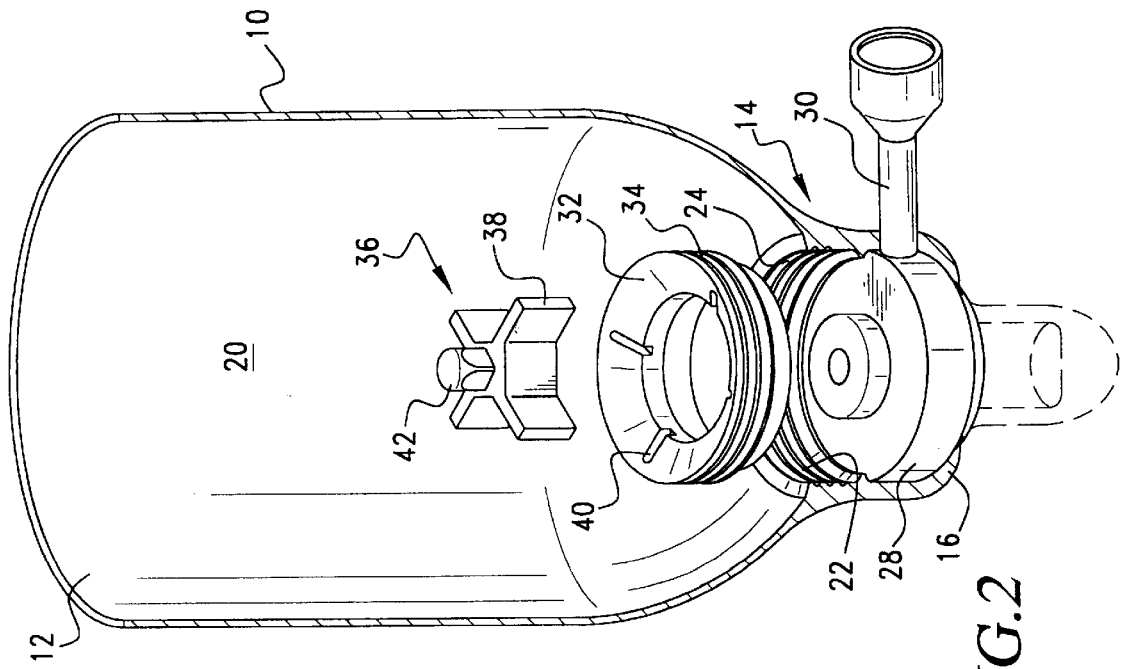
FIG. 1 is a vertical section view of a prosthetic socket having a prosthetic socket component recess and integral threads molded into an opening that provides access to the recess.

With reference to FIG. 1, a prosthetic socket 10 that may be cast, molded, laminated or otherwise formed of synthetic and reinforced components in accordance with known technology to receive the residual limb of an amputee (not shown) within the open end 12 of the prosthetic socket. The prosthetic socket 10 is rigid and is capable of carrying appropriate loads imposed on the socket by an amputee. The socket 10 can be shaped at its open end to accommodate a below the knee amputee or an above the knee amputee. This socket may be lined with an appropriate low friction fabric (not shown) and may include an outer cover (not shown) if desired.

The socket 10 is shaped so that at its closed, distal end 14 it is provided with a prosthetic socket component recess 16 configured and dimensioned so as to receive therein a prosthetic socket component such as a ratchet or other type pin interlock arrangement in a manner to be described below. An appropriate opening 18 may be provided in the side wall of the prosthetic socket device adjacent the recess 16 to accommodate a release actuator rod for a ratchet or other pin interlock system, an example of which will be described below.

The prosthetic socket 10 defines a primary volume 20 for receiving a residual limb of an amputee. Between the primary volume 20 and recess 16 there is provided a preferably circular access opening 22 that includes integrally molded helical threads 24, in accordance with the preferred embodiment of the invention, that extend over a length of the opening 22. The opening 22 provides access to the recess 16 in the distal end of the prosthetic socket 10.

If desired, a chamber 26 may be molded into the distal end of the prosthetic socket 10 as an extension of the recess 16 to accommodate, for example, a lock pin used with a lock pin interlock device (see FIG. 2) that may be placed in the recess 16 in a manner to be described below.

Figure 2:
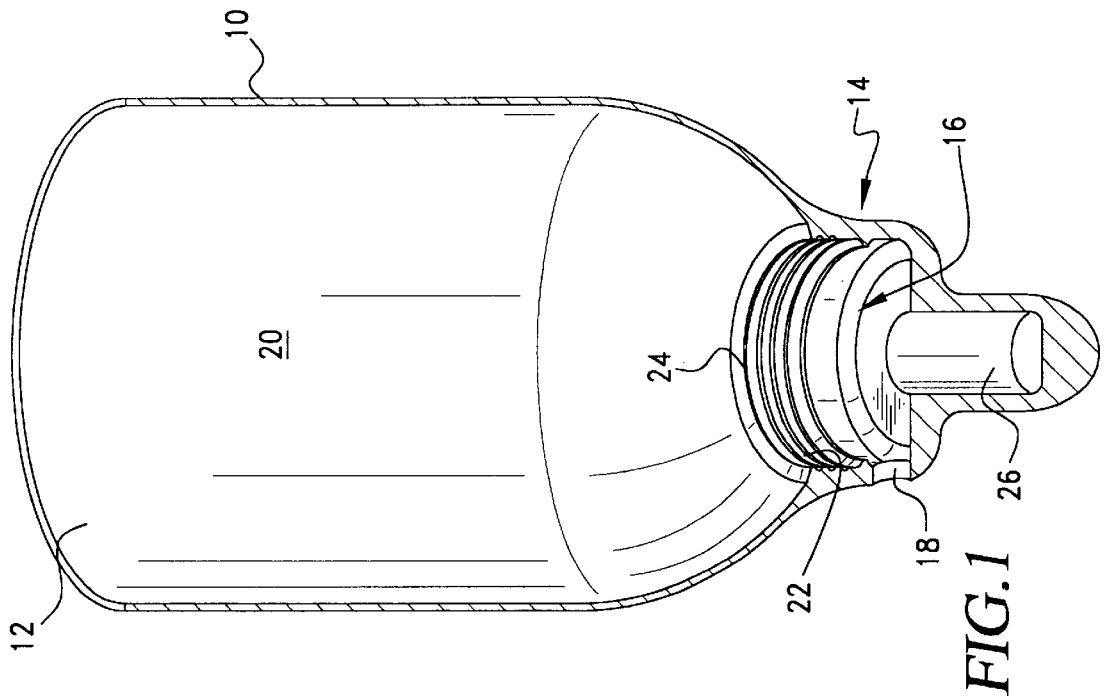
FIG. 2 is an isometric cutaway view showing a prosthetic socket component within a recess molded into the distal end of a prosthetic socket and a retainer nut to be threaded into a threaded circular opening that provides access to the prosthetic socket component recess.

In FIG. 2 the prosthetic socket 10 shown in FIG. 1 is illustrated with a ratchet lock pin type interlock device 28 that has been placed within the recess 16 at the distal end 14 of the prosthetic socket 10. The interlock device 28 is placed in the recess 16 prior to assembly with the lock pin release rod 30 which is inserted through opening 18 and assembled with the interlock device 28 after the latter has been placed in the recess 16.

Alternatively, the interlock device 28 may include a lock pin system (not shown), as taught by U.S. Pat. Nos. 5,928, 290, 6,093,210 and 6,235,062. The lock pin system includes a fastening device having a cylindrical channel and inclined washer dimensioned and configured to accommodate insertion of a pin with minimal resistance. The lock pin system permits rotation of the pin while still securely fastening the pin within the fastening device to prevent unlocking of the pin from the cylindrical channel.

After the device 28 has been placed in recess 16 and assembled with the lock release rod 30, a cylindrical retainer 32 having external threads 34 is threaded into the opening 22 with the threads 34 in mating engagement with threads 24 in the opening 22.

A retainer driver 36 may be utilized for engaging and advancing the retainer 32 via the threads 34,24 into securing engagement with the interlock device 28. The retainer driver 36, for example, may include male protrusions 38 that engage female slots or recesses 40 in the retainer 32 and a hex head 42 that permits engagement by a socket wrench tool. Torque applied to the head 42 when the protrusions 38 are in engagement with slots 40 will result in rotation of the retainer 32 to advance the retainer, when rotated in one direction, into locking or securing engagement with the device 28 or, when rotated in the reverse direction, will permit removal of the retainer 32 and subsequent removal of the device 28 from the recess 16 by reversing the assembly procedure described above.

It should be understood that the chamber 26 is optional and the distal end 14 of the prosthetic socket 10 may be molded or otherwise formed without such appendage.

The device 28 may be substituted by a valve device (not shown) providing communication between the primary volume 20 and the exterior of the prosthetic socket 10 or may include any other appropriate device normally associated with prosthetic sockets at their distal ends. For example a lanyard arrangement (not shown) may be incorporated in the recess with an appropriate opening being formed in the distal end of the prosthetic socket to enable the lanyard to extend from the recess 16 to a region exterior of the primary volume 20.

While helical threads 24 are illustrated as a coupling arrangement for enabling the retainer 32 to be connected with the prosthetic socket 10, it will be understood that any other appropriate coupling arrangement could be utilized, including a quick disconnect arrangement similar to a familiar bayonet type socket for an automotive light bulb or any other appropriate connection that will enable securement of the retainer 32 within the prosthetic socket 10 at a position whereat a prosthetic socket component may be secured in the recess area 16 at the distal end of the socket.

While the recess 16 is illustrated as an annular or circular opening, it will be understood that the recess could be of any appropriate shape that is dimensioned and configured to receive a desired prosthetic socket component to be retained in the recess 16 by a retainer 32.

Figure 3:
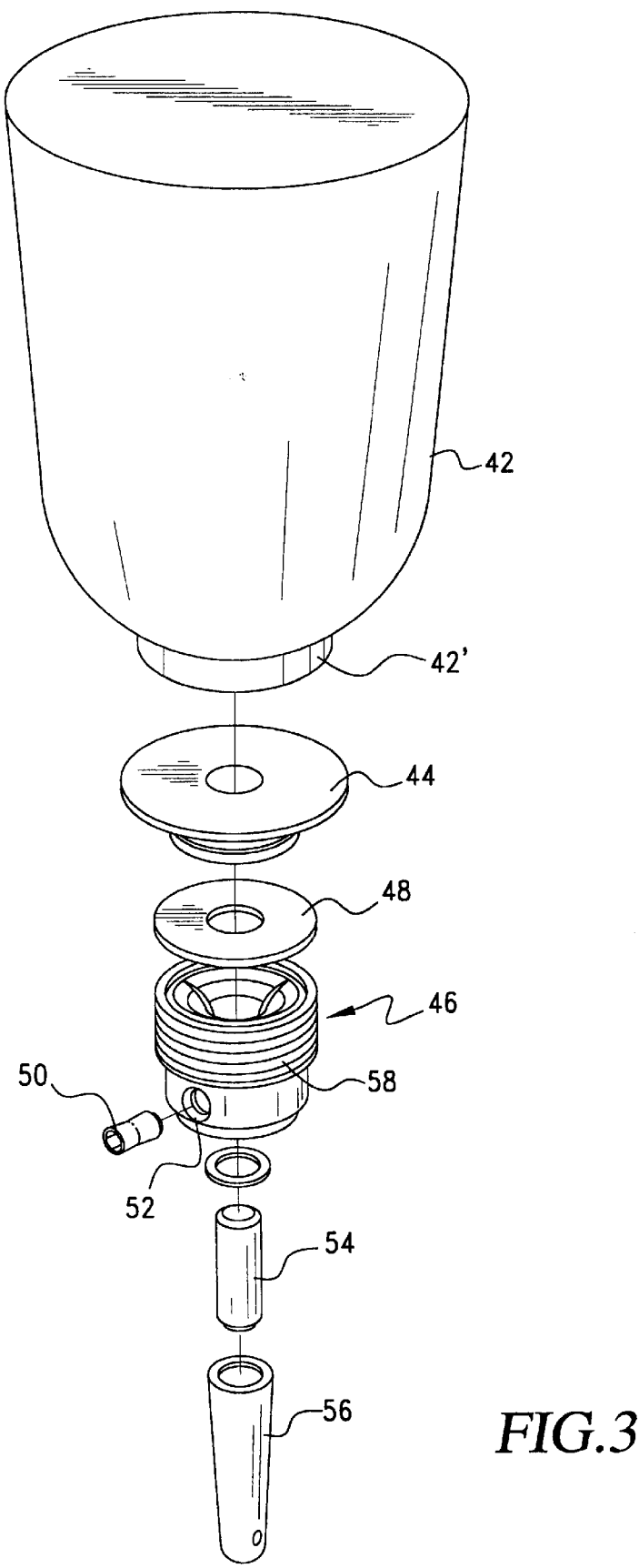
FIG. 3 shows a mold device and mold components that may be used to form the prosthetic socket shown in FIG. 1.
Figure 5:
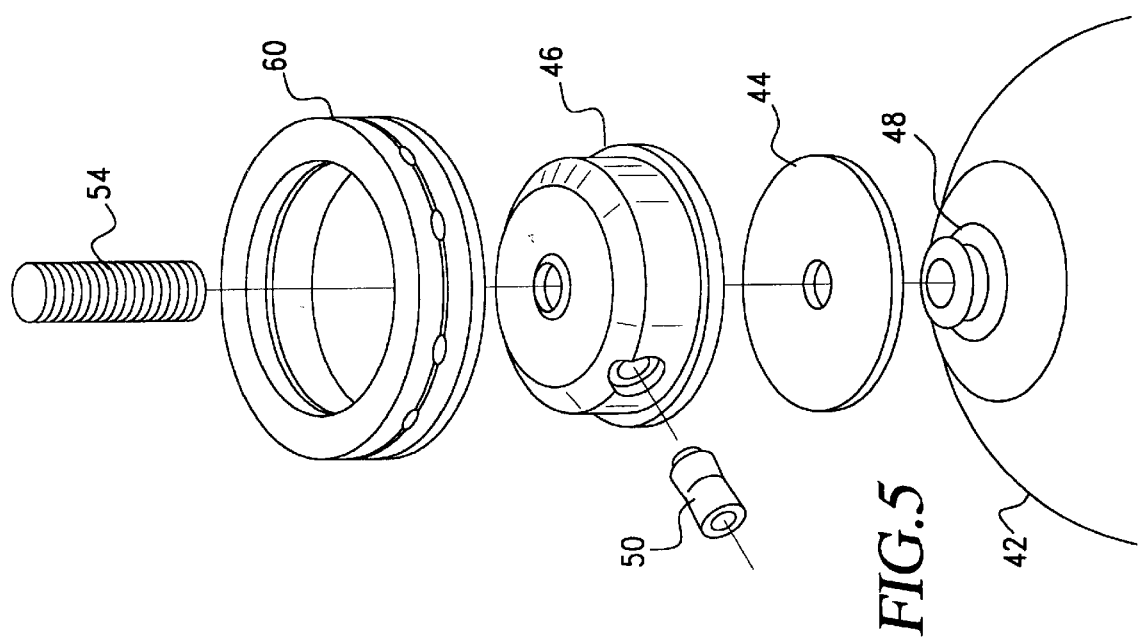
FIG. 5 shows a mold device and mold components used to form the prosthetic socket shown in FIG. 4.

The prosthetic socket 10 with its associated recess 16, access opening 22 and threads 24 may be formed by, for example, laminating or molding prosthetic socket material over a mold 42 as shown in FIG. 3 that has been previously shaped to conform to the exterior profile of the residual limb of an amputee in accordance with known prosthetic procedures. A metallic guide 44 is fastened to the distal end 42' of mold 42 by an appropriate fastener such as double sided adhesive tape. A male plug element 46 is assembled with the guide 44 and a washer 48 may be used to seal the interior of the plug 46 against leakage of unsecured prosthetic socket material into the plug 46. A mold plug 50 is inserted into lateral opening 52 in plug 46 and additional mold plugs 54,56 are assembled to the distal end of the plug 46. This entire assembly then forms a male mold over which appropriate prosthetic socket material is molded, laminated or otherwise applied and subsequently cured into a rigid, load bearing material as illustrated in FIGS. 1 and 2.

The various mold plug elements 46,50,54 and 56 may be configured to provide cavity shapes in the distal end of a prosthetic socket that will accommodate various desired socket component at the distal end of the socket. In the embodiment illustrated in FIG. 3, for example, the plug 46 includes external threads 58 that will be used to mold integral threads 24 in opening 22 of the prosthetic socket shown in FIG. 1. The mold plug 56 is utilized to provide the internal contours of the chamber 26 and the plug 50 will be used to provide the opening 18 when the material used to form the prosthetic socket 10 is molded or laminated over the mold 42 and the plug components illustrated.

While threads 46 are shown on mold plug 58, it will be understood that any other appropriate male or female profile may be provided on the plug 58 in accordance with any desired coupling arrangement that may be desired between the retainer 32 and the prosthetic socket 10. Also, while preferably the threads or other connection system associated with the retainer 32 and opening 22 are integrally molded of socket materials or other curable components of the socket, such threads or connection system could be formed as a subassembly molded or otherwise secured into the distal end of the socket.

Figure 4:
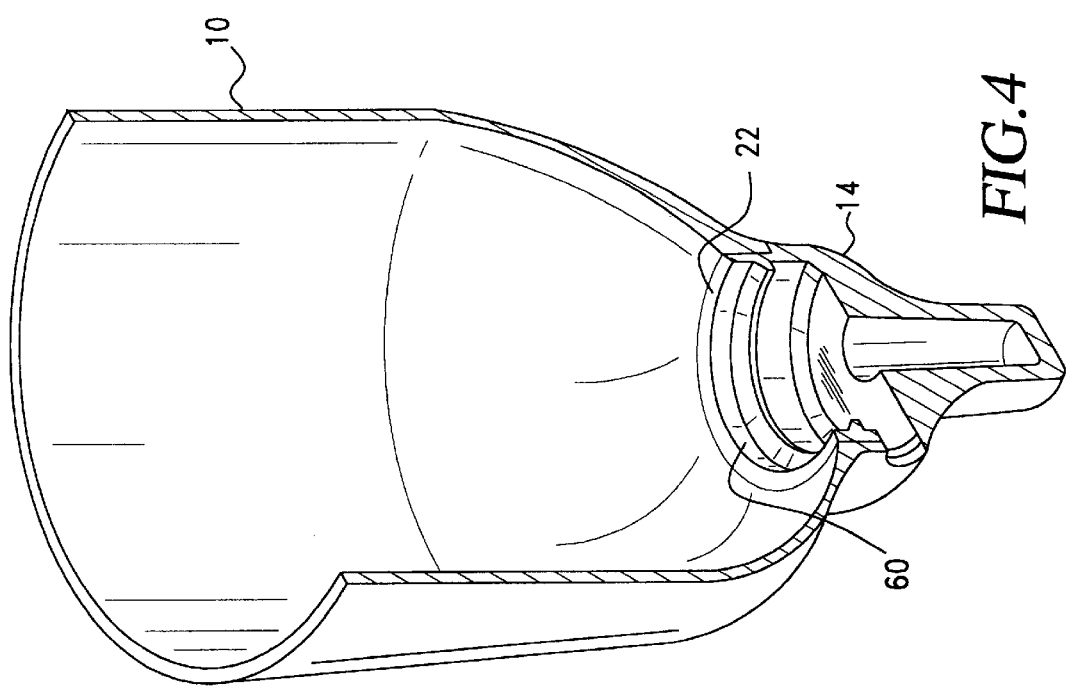
FIG. 4 is a vertical section view of another embodiment of the prosthetic socket of FIG. 1 including a fabrication ring secured to the opening providing access to the recess.

FIG. 4 shows an alternative embodiment of the prosthetic socket 10 of FIG. 1 and further includes a fabrication ring 60 embedded and secured by the prosthetic socket 10 for replacing the integral threads 24 formed in the opening 22 of the prosthetic socket of FIG. 1. The secured fabrication ring 60 enables easier removal of the plug 46. The components used to form the prosthetic socket 10 of FIG. 4 are similar to the components used in FIG. 3 with the addition of the fabrication ring 60.

Figure 6:
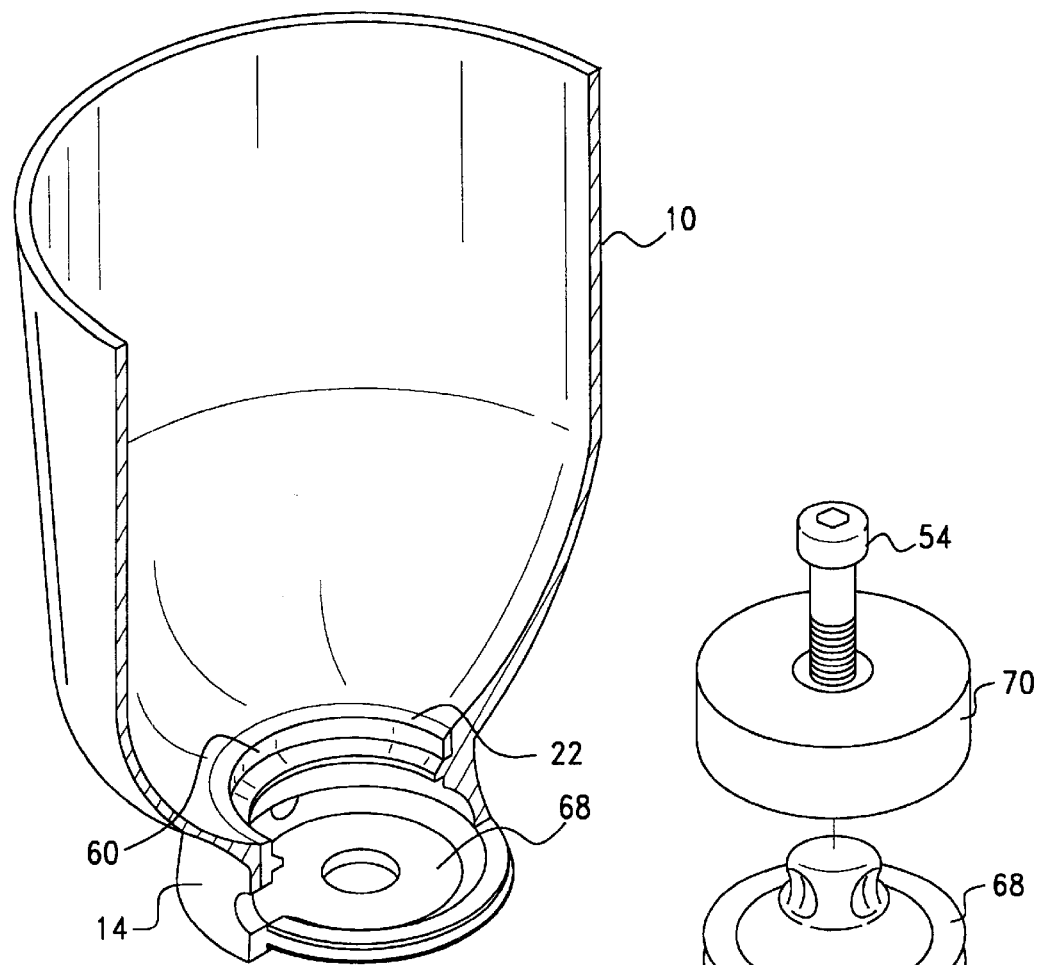
FIG. 6 is a vertical section view of another embodiment of the prosthetic socket of FIG. 1 including a fabrication ring and a pyramid coupling secured to the prosthetic socket at the distal end.
Figure 7:
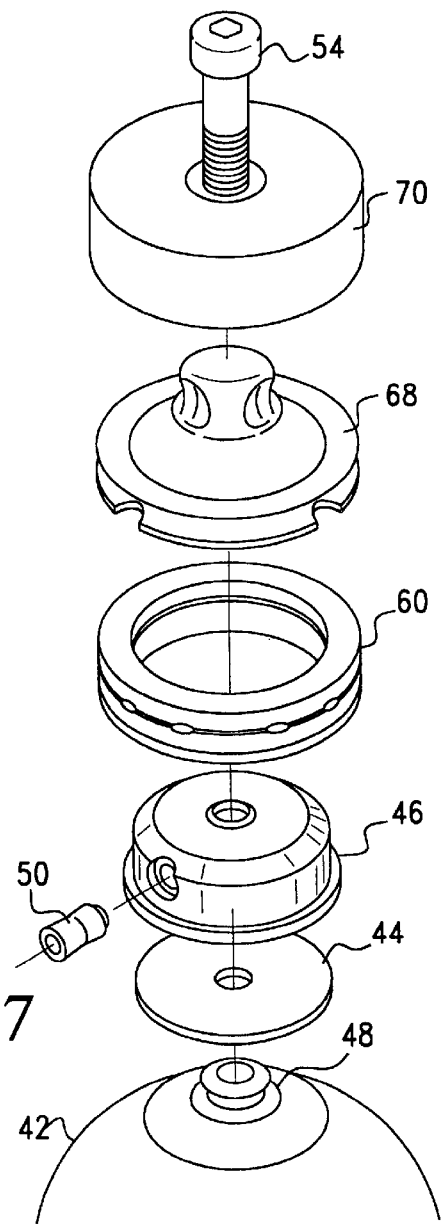
FIG. 7 shows a mold device and mold components used to form the prosthetic socket shown in FIG. 6.

In another alternative embodiment of the prosthetic socket of FIG. 1, FIG. 6 shows the prosthetic socket 10 including a pyramid coupling 68. The prosthetic socket 10 includes a fabrication ring 60 that replaces the integral threads 24 formed in the opening of the prosthetic socket of FIG. 1 and a pyramid coupling 68 disposed in the recess area 16 at the distal end of the socket. FIG. 7 illustrates the components used to form the prosthetic socket 10 shown in FIG. 6. The components used to form the prosthetic socket 10 of FIG. 6 are similar to the components used in FIG. 3 and further include the pyramid coupling 68, a pyramid cap 70 and a fabrication ring 60.

Figure 8:
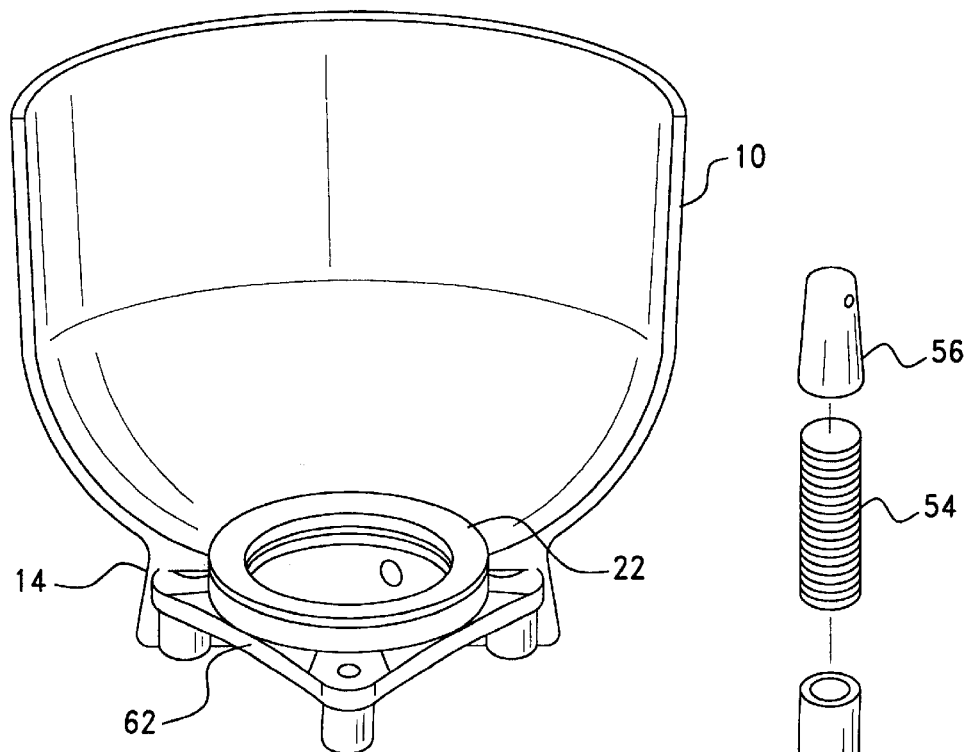
FIG. 8 is a vertical section view of another embodiment of the prosthetic socket of FIG. 1 including a four-hole coupling secured to the prosthetic socket at the distal end.
Figure 9:
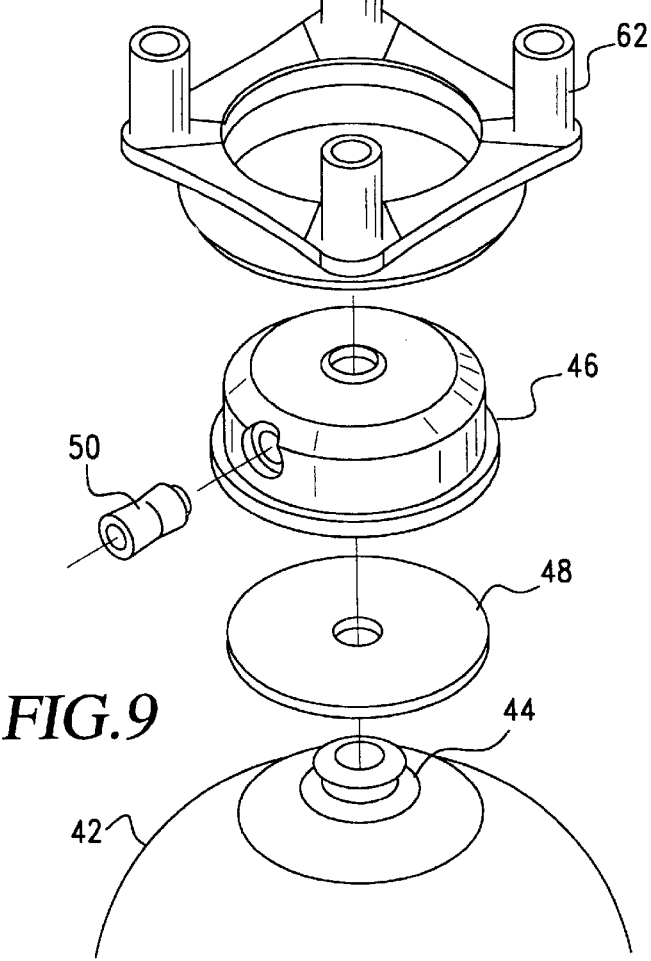
FIG. 9 shows a mold device and mold components used to form the prosthetic socket shown in FIG. 8.

In another alternative embodiment of the prosthetic socket of FIG. 1, FIG. 8 shows a prosthetic socket 10 having a 4-hole adapter 62 disposed and secured in the recess area 16 at the distal end 14 of the prosthetic socket 10. The 4-hole adapter 62 is threaded internally and also replaces the integral threads 24 formed in the opening 22 of the prosthetic socket of FIG. 1. FIG. 9 illustrates the components used to form the prosthetic socket 10 shown in FIG. 8. The components used to form the prosthetic socket 10 of FIG. 8 are similar to the components used in FIG. 3 and further includes the 4-hole adapter 62.

It is to be understood that a preferred embodiment of the invention has been described and that various modifications thereto may be made by persons skilled in the art without departing from the spirit and scope of the invention as defined in the following claims.

What is claimed is:

1. A prosthetic socket comprising a proximal open end, a primary volume and a distal end; said distal end including a recess configured to receive a prosthetic socket component; an access opening between the primary volume and the recess; said access opening configured for receiving a removable retainer for a prosthetic socket component located in the recess, and including a coupling arrangement configured to cooperate with the removable retainer.

2. The prosthetic socket as claimed in claim 1, wherein said access opening is circular and said coupling arrangement comprises helical threads.

3. The prosthetic socket as claimed in claim 1, including a prosthetic socket component located within said recess and a removable retainer in coupling engagement with said coupling arrangement located in said access opening at a position whereat the prosthetic socket component is removably retained in said recess.

4. The prosthetic socket as claimed in claim 3, wherein said coupling arrangement comprises helical threads and wherein said retainer device includes helical threads configured to cooperate with the helical threads in the access opening whereby, upon engagement between the helical threads of the retainer and the helical threads of the access opening, the retainer device may be advanced through the opening by rotation thereof into engagement with the prosthetic socket component or for removal from the opening for removably retaining the prosthetic socket component in said recess.

5. The prosthetic socket device as claimed in claim 4, wherein said retainer device includes at least one driving slot opening into said primary volume, said slot being arranged to receive a driver having at least one protrusion configured to engage said slot.

6. The prosthetic device as claimed in claim 5, wherein said prosthetic socket component is selected from the group consisting of a ratchet lock pin receiving and locking device, a lanyard arrangement or and a valve device.

7. The prosthetic socket as claimed in claim 2, wherein said helical threads are molded in one integral piece with said side wall.

8. The prosthetic socket as claimed in claim 1, wherein said access opening is circular and said coupling arrangement comprises helical threads, wherein said coupling arrangement includes a fastener ring embedded within said access opening and forming said helical threads.

9. The prosthetic socket as claimed in claim 1, including said prosthetic socket component being located within said recess and a removable retainer coupling engagement with said coupling arrangement located in said access opening whereat the prosthetic socket component is removably retained in said recess.

10. The prosthetic socket as claimed in claim 9, wherein said coupling arrangement further includes a pyramid adapter secured by said prosthetic socket at said distal end and adapted to cooperate with said removable retainer.

11. The prosthetic socket as claimed in claim 1, wherein said coupling arrangement includes a four-hole adapter having internal threads and secured at the distal end to said prosthetic socket, said four-hole adapter forming said recess and said access opening.

12. The prosthetic socket as claimed in claim 10, including said prosthetic socket component being located within said recess and a removable retainer coupling engagement with said coupling arrangement located in said access opening whereat the prosthetic socket component is removably retained in said recess.

* * * * *